United States Patent
Tremulis et al.

(10) Patent No.: US 8,961,532 B2
(45) Date of Patent: Feb. 24, 2015

(54) ATRAUMATIC CATHETER TIP

(75) Inventors: W. Stephen Tremulis, Minnetrista, MN (US); Kevin R. Arnal, Excelsior, MN (US); Jeffrey P. Callister, Deephaven, MN (US); James R. Mujwid, Crystal, MN (US); John Fritz Otte, St. Anthony, MN (US); Lori Garlie, Carver, MN (US)

(73) Assignee: Bayer Essure Inc., Milpitas, CA (US)

( * ) Notice: Subject to any disclaimer, the term of this patent is extended or adjusted under 35 U.S.C. 154(b) by 1264 days.

(21) Appl. No.: 11/619,979

(22) Filed: Jan. 4, 2007

(65) Prior Publication Data

US 2007/0219466 A1 Sep. 20, 2007

Related U.S. Application Data

(60) Provisional application No. 60/756,910, filed on Jan. 6, 2006.

(51) Int. Cl.
*A61F 11/00* (2006.01)
*A61M 25/00* (2006.01)

(52) U.S. Cl.
CPC ....... *A61M 25/0069* (2013.01); *A61M 25/0068* (2013.01); *A61M 25/008* (2013.01); *A61M 25/0082* (2013.01); *A61M 2025/0081* (2013.01)
USPC ............ 606/108; 606/157; 606/191; 606/193

(58) Field of Classification Search
CPC ..................... A61M 25/0068; A61M 25/0069; A61M 25/0082; A61M 25/008; A61M 2025/008; A61M 6/146; A61M 6/225
USPC ...................... 623/1.11, 1.12, 1.18, 1.2, 1.23; 606/108, 157, 191, 193; 604/523, 525, 604/510, 528; 128/200.26, 838, 840, 843, 128/831–832; 600/105
See application file for complete search history.

(56) References Cited

U.S. PATENT DOCUMENTS

| | | | | |
|---|---|---|---|---|
| 2,862,498 A | * | 12/1958 | Weekes .................... | 128/207.14 |
| 3,710,777 A | * | 1/1973 | Sparks ............................ | 600/36 |
| 3,754,554 A | * | 8/1973 | Felbarg .................... | 128/200.26 |
| 3,884,242 A | * | 5/1975 | Bazell et al. ............. | 128/207.15 |
| 4,819,619 A | * | 4/1989 | Augustine et al. ........ | 128/200.26 |
| 5,207,232 A | * | 5/1993 | Shihata ......................... | 128/837 |
| 5,273,527 A | * | 12/1993 | Schatz et al. .................... | 604/43 |
| 5,685,824 A | * | 11/1997 | Takei ............................. | 600/135 |
| 5,720,275 A | * | 2/1998 | Patil et al. ................ | 128/200.26 |
| 5,791,341 A | * | 8/1998 | Bullard .................... | 128/207.15 |
| 5,873,362 A | * | 2/1999 | Parker ...................... | 128/207.14 |
| 6,096,052 A | | 8/2000 | Callister et al. | |
| 6,432,116 B1 | | 8/2002 | Callister et al. | |
| 2001/0021840 A1 | * | 9/2001 | Suresh et al. ................. | 604/525 |
| 2002/0055771 A1 | * | 5/2002 | Sandock .................... | 623/1.23 |
| 2003/0149467 A1 | * | 8/2003 | Linder et al. ................. | 623/1.11 |
| 2005/0045183 A1 | * | 3/2005 | Callister et al. ............... | 128/831 |
| 2005/0209676 A1 | * | 9/2005 | Kusleika ...................... | 623/1.11 |
| 2006/0276808 A1 | * | 12/2006 | Arnal et al. ................... | 606/148 |

* cited by examiner

*Primary Examiner* — David Eastwood
(74) *Attorney, Agent, or Firm* — Blakely, Sokoloff, Taylor & Zafman LLP

(57) ABSTRACT

A delivery system for delivering an occluding device to a body lumen comprises an elongated shaft having a proximal end and a distal end, a delivery means for delivering the occluding device to a desired location within the body lumen, and a flexible atraumatic tip on the distal end of the elongated shaft. The distal end of the elongated shaft is insertable into the body lumen. The atraumatic tip is configured to guide the elongated shaft through the body lumen while avoiding perforation of the body lumen.

17 Claims, 7 Drawing Sheets

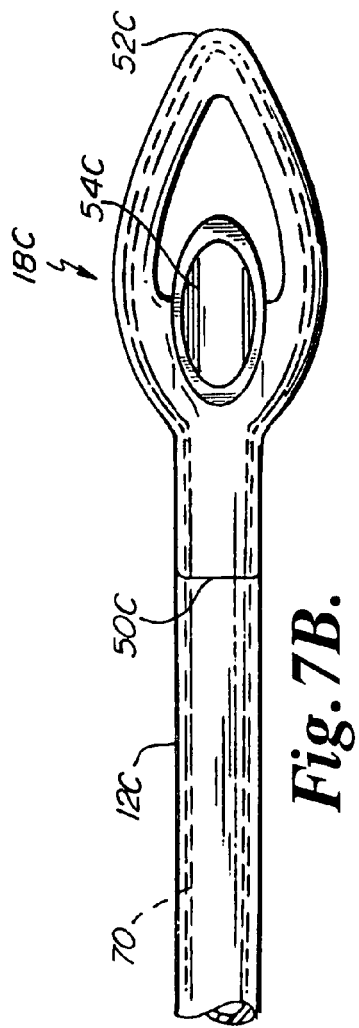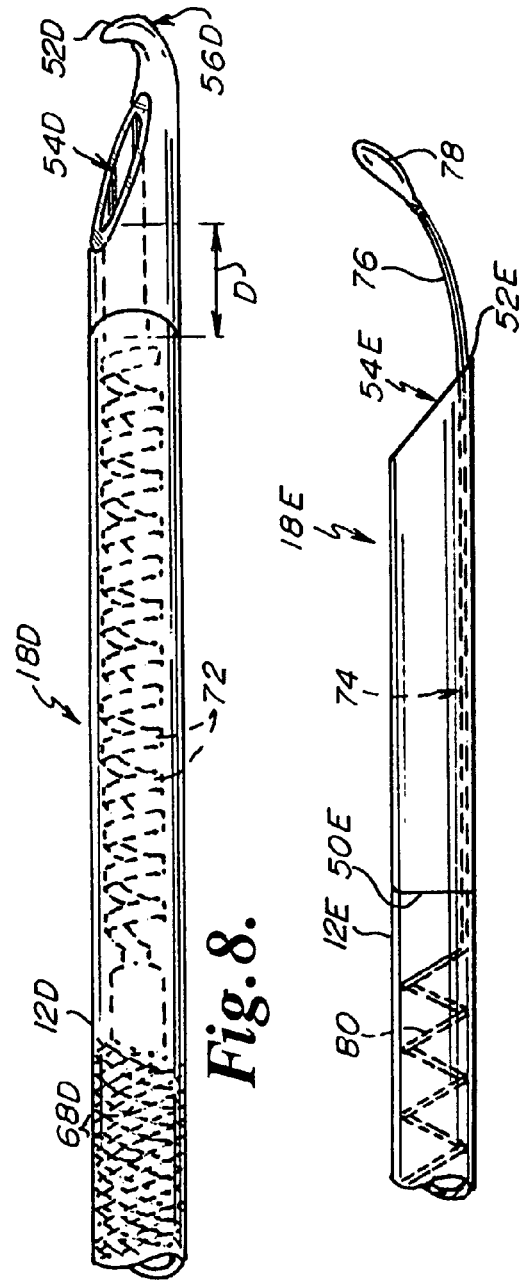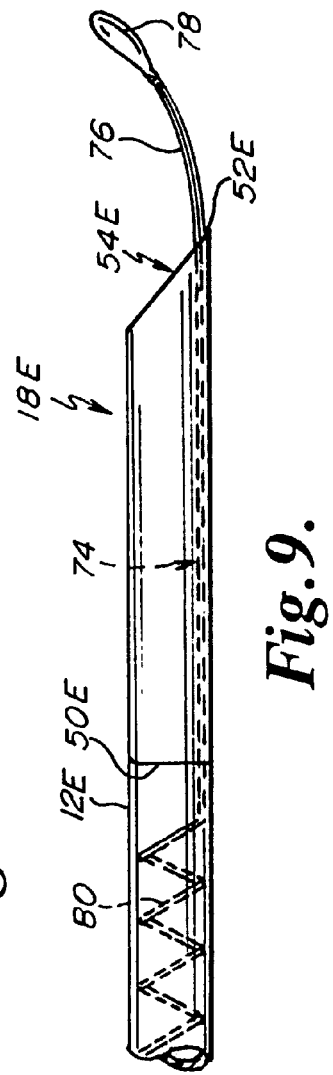
*Fig.7B.* *Fig.8.* *Fig.9.*

ATRAUMATIC CATHETER TIP

CROSS REFERENCE TO RELATED APPLICATION

This application is based on and claims the benefit of U.S. Provisional Application No. 60/756,910, filed Jan. 6, 2006, the entirety of which is hereby incorporated by reference

FIELD OF THE INVENTION

The present invention relates to medical catheters and, more particularly, to delivery catheters for delivering an occluding device to an internal body lumen.

BACKGROUND OF THE INVENTION

U.S. Pat. Nos. 6,096,052 and 6,432,116 each entitled "Occluding Device and Method of Use" describe a device for occluding a body lumen. Each of the noted U.S. patents is hereby incorporated by reference. The patents particularly describe a contraceptive or sterilization device for occluding a reproductive tract or lumen to prevent the passage of reproductive cells through the tract or lumen. The device generally comprises a tubular member and a mesh member transversely disposed on the tubular member lumen. The mesh member is permeable to allow for tissue ingrowth, which produces a tissue impregnated mesh occluding the body lumen. The occluding device of the invention can be used in the fallopian tubes of a female patient, the vas deferens of a male patient, or various other body lumens. The device can additionally be used for delivering drugs or other substances to the bodies of human or animal subjects.

The device is typically delivered into the lumen of an anatomical passageway via use of an endoscope and, in the instance of a fallopian tube, via the use of a hysteroscope. A hysteroscope enables a physician to look and operate inside the uterus with a small camera; a working channel is provided within the hysteroscope. In the instance of placing the occluding device in a fallopian tube, the tubal ostium of the uterus must be visualized with a flexible or rigid scope. Because the opposing walls of the uterus are normally pressed together, the physician must deliver fluid to the uterus under pressure through a port in the scope to separate the uterine walls. To deliver the catheter, the working channel in the scope must be opened up and the delivery catheter inserted. The fallopian tube is located at an angle off of the uterus requiring the delivery catheter of the occluding device to bend and conform to the path of the fallopian tube. In doing so, it is possible for the blunt end tip of the delivery catheter to perforate the tissue and/or present the occluding device in a sub-mucosal placement.

Therefore, there is a need for a delivery system having a tip that reduces the opportunity for perforation or sub-mucosal placement ("parallel placement") of the occluding device.

BRIEF SUMMARY OF THE INVENTION

The present invention solves the foregoing problems by providing a delivery system for delivering an occluding device to a body lumen, the delivery system comprising an elongated shaft having a proximal end and a distal end, a delivery means for delivering the occluding device to a desired location within the body lumen, and a flexible atraumatic tip on the distal end of the elongated shaft. The distal end of the elongated shaft is insertable into the body lumen. The atraumatic tip is configured to guide the elongated shaft through the body lumen while avoiding perforation of the body lumen.

The atraumatic tip has a proximal end and a distal end, and may include a slanted facial opening near the distal end of the tip. Furthermore, the atraumatic tip may also include a guide member at the distal end of the atraumatic tip for improved deflection of the tip so as to avoid perforation of the body lumen.

BRIEF DESCRIPTION OF THE DRAWINGS

FIG. 7B is a top view of the atraumatic tip illustrated in FIG. 7A.

FIG. 8 is a side view of a fourth alternative embodiment of an atraumatic tip in accordance with the present invention reinforced with a coil member.

FIG. 9 is a side view of a fifth alternative embodiment of an atraumatic tip in accordance with the present invention having a guide wire extending from a distal end of the tip.

DETAILED DESCRIPTION OF THE INVENTION

The present invention comprises an atraumatic tip that is configured to work with a delivery system for an occluding device that is delivered into a body lumen. The occluding device may be delivered to, for example, a fallopian tube through the working channel of a hysteroscope, or the vas deferens through the working channel of an endoscope. For purposes of explanation, the present invention will be described in reference to delivery systems configured to deliver occluding devices to the fallopian tubes. However, one skilled in the art will appreciate that occluding devices may be delivered into numerous other body lumens without departing from the intended scope of the present invention. The atraumatic tip of the present invention substantially minimizes the risks of uterine or fallopian tube perforations and the risks of sub mucosal placement of the occluding device.

Figure 1:
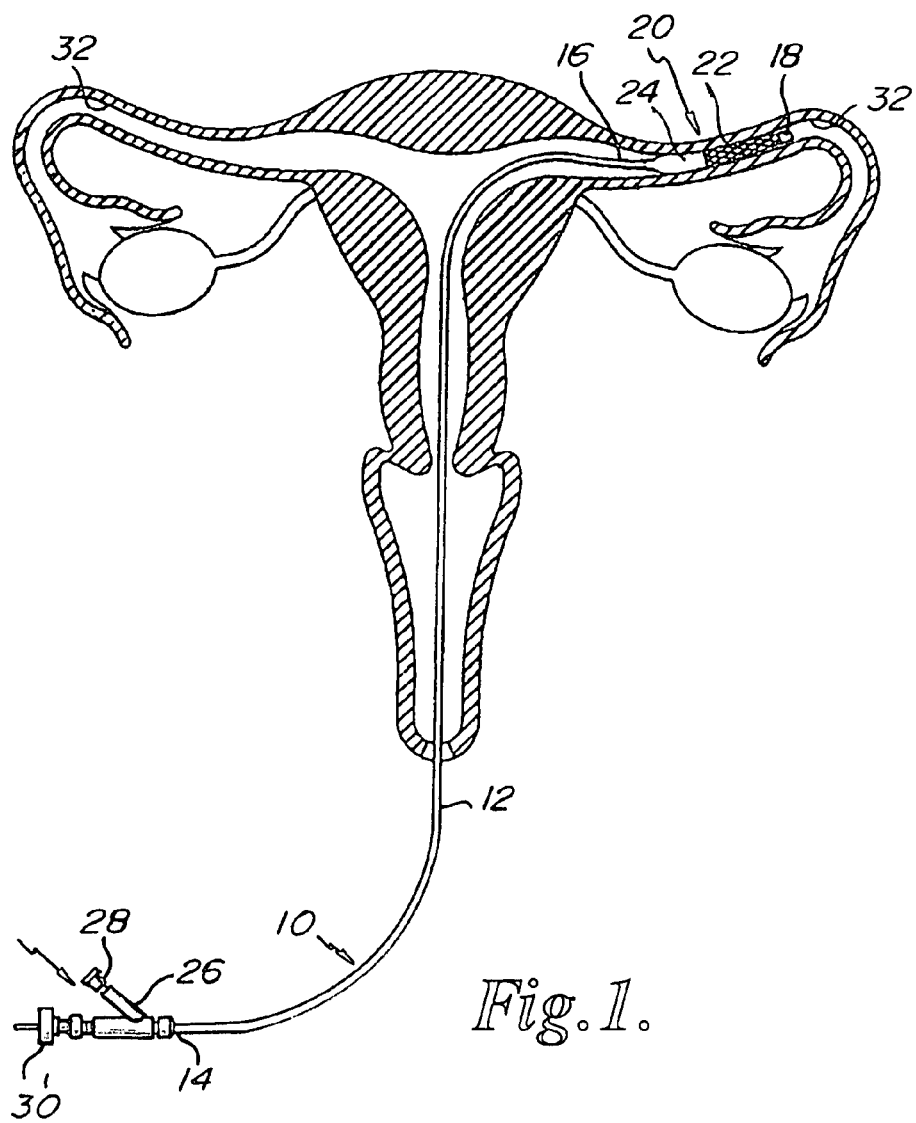
FIG. 1 is a diagram illustrating a first delivery system delivering an occluding device to a desired location within the female reproductive anatomy.

FIG. 1 is a diagram illustrating delivery system 10 in accordance with the present invention delivering an occluding device to a desired location within the female reproductive anatomy. Delivery system 10 includes elongated shaft 12 having proximal end 14 and distal end 16, atraumatic tip 18, occluding device 20 having tubular member 22 with a relatively small transverse dimension, inflatable member 24, and adapter 26 having first port 28 and second port 30. In particular, and as shown in FIG. 1, occluding device 20 is mounted on inflatable member 24 of delivery system 10 and positioned within fallopian tube 32.

The practice of delivering occluding device 20 comprises the following general steps, with specific reference to the embodiment illustrated in FIG. 1. First, occluding device 20 is mounted onto an outer surface of inflatable member 24, and delivery system 10 is advanced under fluoroscopic, hysteroscopic, or ultrasonic visualization until tubular member 22 of occluding device 20 is positioned at a target location within one of fallopian tubes 32. Inflation fluid may then be introduced through first port 28 of adapter 26 to inflate inflatable member 24. Inflation of inflatable member 24 expands tubular member 22 to an expanded position, lodging it in fallopian tube 32. Inflatable member 24 is then deflated and delivery system 10 removed, leaving expanded tubular member 22 implanted within fallopian tube 32. After being in the expanded position within fallopian tube 32 for a period of time, tubular member 22 of occluding device 20 epithelializes to secure occluding device 20 within the tube. Over time, tissue ingrowth in a mesh member (not shown in FIG. 1) of occluding device 20 will occlude fallopian tube 32, thereby rendering occluding device useful as a contraceptive means.

Figure 2:
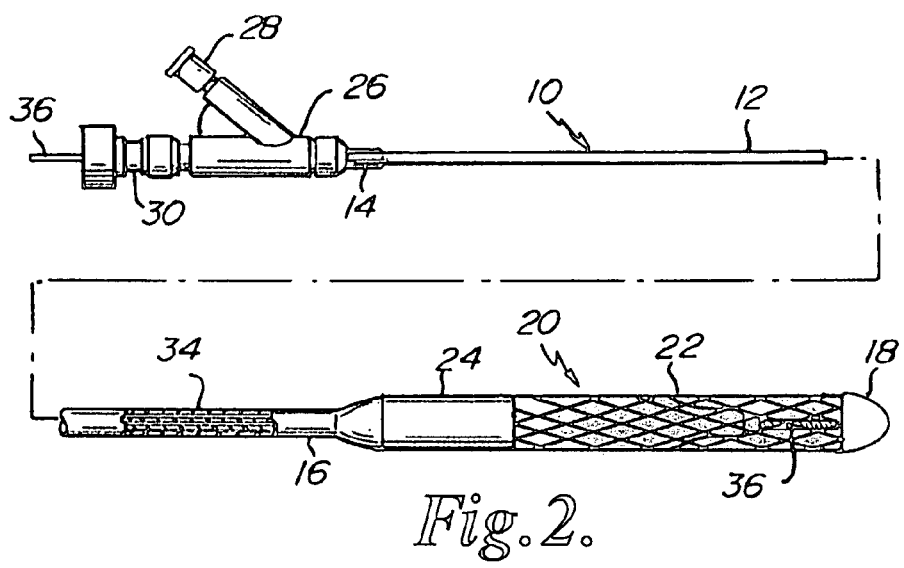
FIG. 2 is side view of the delivery system of FIG. 1 illustrating an atraumatic tip in accordance with the present invention.

FIG. 2 is a side broken view of delivery system 10 in accordance with the present invention. In particular, FIG. 2 illustrates delivery system 10 incorporating atraumatic tip 18 of the present invention. Delivery system 10 further includes inflation lumen 34 in fluid connection with inflatable member 24 mounted near distal end 16 of elongated shaft 12. Occluding device 20 may be mounted on inflatable member 24, and preferably closely conforms to the diameter of inflatable member 38 when in an uninflated position to facilitate introduction of occluding device 20 into the desired body lumen. If necessary, tubular member 22 may be deformed to facilitate mounting onto inflatable member 24.

As shown in FIG. 2, a guidewire 36 may be extended into second port 30 of adapter 26 and through the mesh member within tubular member 22, provided the guidewire has a relatively small diameter compared with the mesh size. For example, a conventional guidewire having a diameter of about 0.018 inches or less may typically be extended through the mesh member without adversely affecting the mesh member.

In the embodiment shown in FIG. 2, atraumatic tip 18 is coupled to a distal end of inflatable member 24 and has a generally curved outer surface. In particular, atraumatic tip 18 is a blunt end formed from a soft, flexible material capable of deforming as it contacts, for example, an inner wall of fallopian tube 32. As a result of the advantages provided by a curved face and soft material, delivery system 10 is able to guide occluding device 20 while minimizing the risk of perforation of the fallopian tube or sub-mucosal placement of the occluding device. As will be described in further detail to follow, atraumatic tip 18 is merely one example of a tip according to the present invention.

Figure 3:
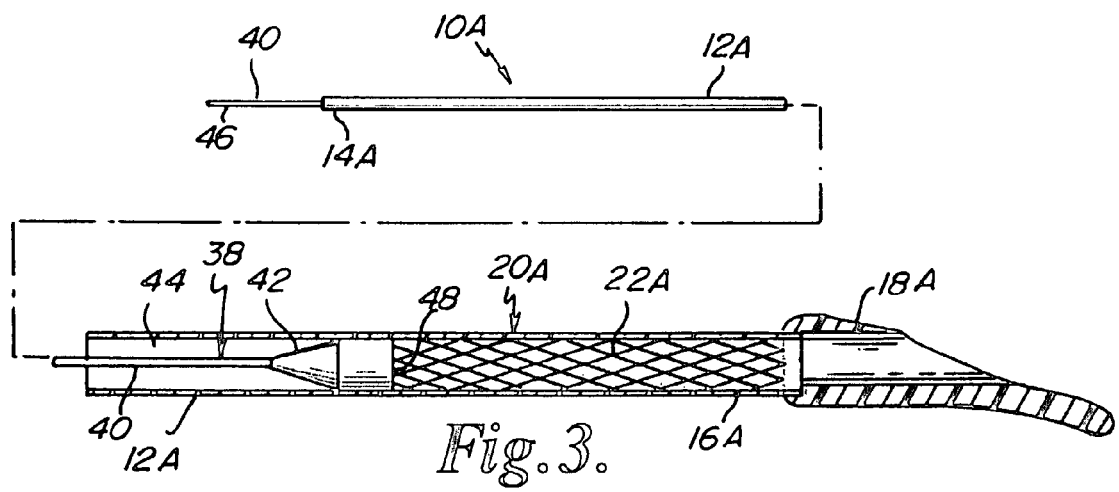
FIG. 3 is a side view of a second type of delivery system illustrating a first alternative embodiment of an atraumatic tip in accordance with the present invention.

FIG. 3 is a side broken view of delivery system 10A in accordance with the present invention having a self-expanding occluding device 20A. Thus, unlike occluding device 20 described above in reference to FIGS. 1 and 2 which required an inflatable balloon member to expand the device, occluding device 20A is designed to expand without the use of an inflatable member. As shown in FIG. 3, delivery system 10A includes elongated shaft 12A having proximal end 14A and distal end 16A, atraumatic tip 18A, occluding device 20A having tubular member 22A, and pusher device 38 having pusher rod 40 and pusher head 42. Pusher device 38 is disposed within lumen 44 defined by an inner surface of elongated shaft 12A. A proximal end 46 of pusher rod 40 extends outside of proximal end 14A of elongated shaft 12A, while face 48 of pusher head 42 is in contact with a proximal end of tubular member 22A. The self expanding tubular member 22A may be deformed into a collapsed position within lumen 44 of elongated shaft 12A, and expanded into an expanded position within the body lumen by longitudinally displacing tubular member 22A out distal end 16A of elongated shaft 12A to thereby remove the radially compressive force of elongated shaft 12A. As shown in FIG. 3, the longitudinal displacement may be performed with pusher device 38 by applying a force on the distal end of tubular member 22A with face 48 of pusher head 42. However, one skilled in the art would appreciate that pusher device 38 is merely one example of a deployment means, and numerous other deployment means are possible and contemplated.

Figure 4A:
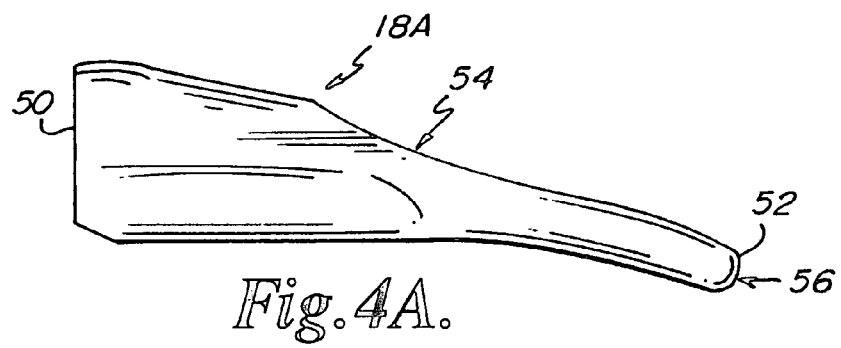
FIG. 4A is a side view of the atraumatic tip illustrated in FIG. 3.
Figure 4B:
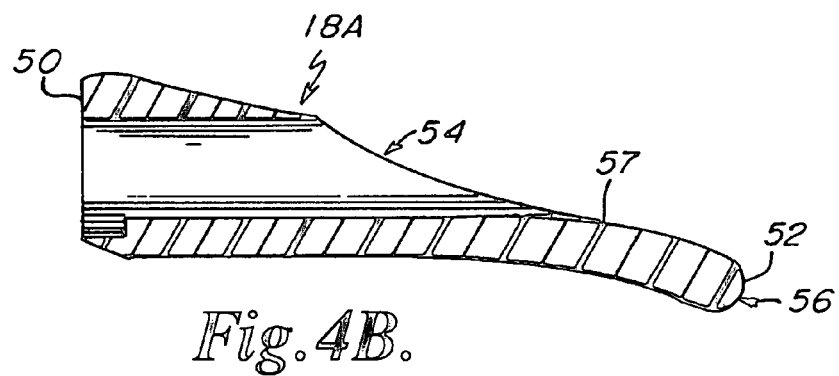
FIG. 4B is a cross-sectional view of the atraumatic tip illustrated in FIG. 3.

FIGS. 4A and 4B illustrate side and cross-sectional views, respectively, of atraumatic tip 18A in accordance with the present invention. As shown in FIGS. 4A and 4B, atraumatic tip 18A includes proximal end 50, distal end 52, slanted facial opening 54, and leading edge 56. Delivery system 10A may be manufactured such that atraumatic tip 18A is formed integral with elongated shaft 12A. Alternatively, and as depicted in FIGS. 4A and 4B, atraumatic tip 18A may be formed separate from elongated shaft 12A and coupled to the shaft during an assembly procedure. When formed separately, proximal end 50 of atraumatic tip 18A is coupled to distal end 16A of elongated shaft 12A by any suitable means of attachment such as, for example, with an adhesive or by heat welding.

Slanted facial opening 54 is sized so as to allow deployment of occluding device 20A from within lumen 44 of elongated shaft 12A as discussed above. Slanted facial opening 54 may be designed in numerous suitable shape configurations. However, slanted facial opening 54 preferably takes on a generally ovoid configuration for improved tip flexibility.

Figure 4C:
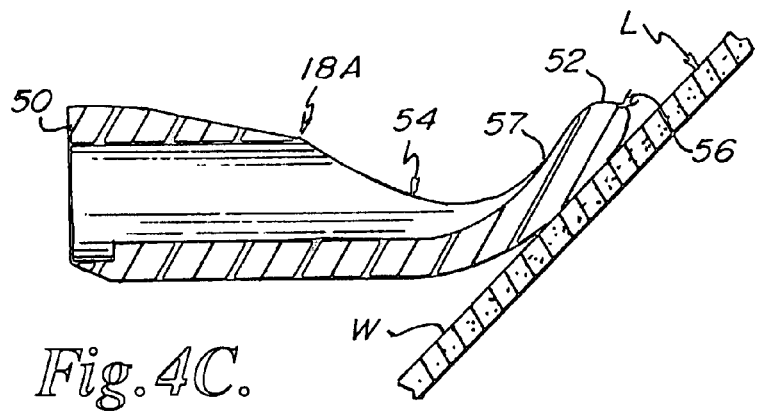
FIG. 4C is a cross-sectional view of the atraumatic tip of FIG. 3 illustrating how the tip is configured to flex when it comes into contact with an inner wall of a body lumen.

Leading edge 56 of atraumatic tip 18A is a blunt end having a generally rounded outer surface. As best seen in FIG. 4B, leading edge 56 is located below a distal end 57 of slanted facial opening 54 such that occluding device 20A is deployed above the leading edge. Atraumatic tip 18A is preferably formed from a material such as, for example, a plastic resin, polyethylene, polyvinylchloride, silicone, or Teflon. As a result, leading edge 56 is soft and flexible, allowing it to bend or flex as it comes into contact with an inner wall of a body lumen so that atraumatic tip 18A does not puncture or otherwise damage the body lumen. The ability of atraumatic tip 18A to flex is illustrated in FIG. 4C. In particular, as shown in FIG. 4C, leading edge 56 has been forced into contact with inner wall W of body lumen L, thereby increasing the surface area of atraumatic tip 18A in contact with inner wall W. The combination of the elongated, slanted facial opening, flexible material, and rounded leading edge below the facial opening allows atraumatic tip 18A to bend about midway up the longitudinal length of slanted facial opening 54, thereby increasing the contact area between atraumatic tip 18A and inner wall W and minimizing the risk of perforation or sub-mucosal placement of occluding device 20A.

Figure 5A:
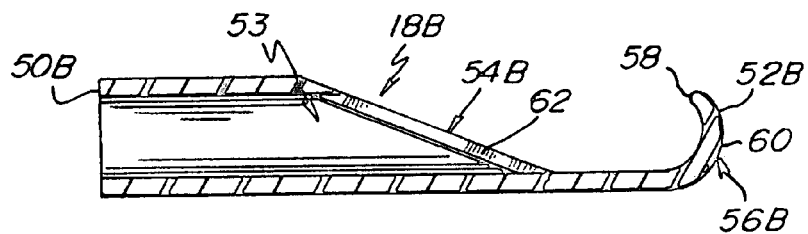
FIG. 5A is a cross-sectional view of a second alternative embodiment of an atraumatic tip in accordance with the present invention having a curved leading edge.
Figure 5B:
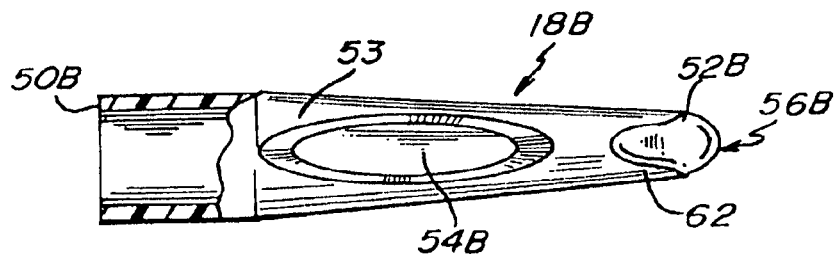
FIG. 5B is a top view of the atraumatic tip illustrated in FIG. 5A.

FIGS. 5A and 5B illustrate cross-sectional and top views, respectively, of atraumatic tip 18B, which is a second alternative embodiment of an atraumatic tip in accordance with the present invention. Atraumatic tip 18B includes proximal end 50B, distal end 52B, central portion 53 having slanted facial opening 54B in an ovoid configuration, and leading edge 56B. Leading edge 56B is designed as a curved flange wherein an end section 58 of leading edge 56B is located proximal to middle section 60 of leading edge 56B. The curved flange configuration of leading edge 56B is designed for improved tip deflection and a lower pressure on atraumatic tip 18B when the tip comes into contact with an inner surface of a body lumen.

Central portion 53 of atraumatic tip 18B is preferably formed from a soft plastic resin, such as a 40 D PEBAX material (a polyether block amine (PEBA) plastic resin). Around central portion 53 of atraumatic tip 18B is an outer portion 62 of the tip having a tapered framework ending in leading edge 56B. Outer portion 62 of atraumatic tip 18B is also preferably formed from a soft plastic resin, such as a 35 D PEBAX material. In operation, atraumatic tip 18B is designed to prolapse or bend over when encountering soft tissues so that the tip does not penetrate or core out tissues in a body lumen, such as the fallopian tubes. In the embodiment shown and described in reference to FIGS. 5A and 5B, the 40 D PEBAX section (central portion 53) helps to prevent the entire tip region from bending over. In other words, atraumatic tip 18B is designed to bend over about halfway up the taper (i.e., the 35 D PEBAX outer portion) and then resist bending at the 40 D PEBAX central portion. As a result, perforations and sub-mucosal placements may be significantly reduced due to the increased surface area in contact with the body lumen as opposed to a more rigid tip that is not designed to bend upon contact with a lumen wall. Although central portion 53 and outer portion 62 were described as preferably being formed from a PEBAX material, other suitable materials, such as those described above in reference to atraumatic tip 18A, are also contemplated.

Figure 6A:
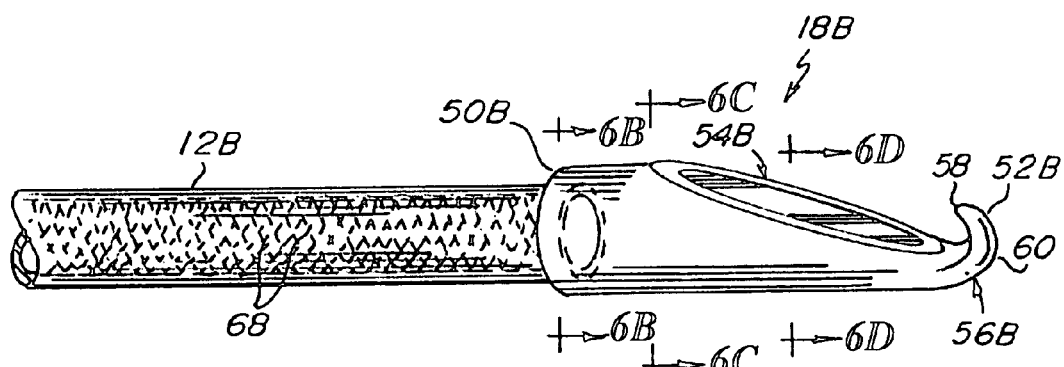
FIG. 6A is a perspective view of the atraumatic tip illustrated in FIG. 5A coupled to an elongated shaft reinforced with a mesh member.
Figure 6B:
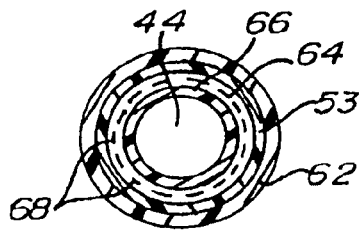
FIGS. 6B-6D illustrate section views of the atraumatic tip illustrated in FIG. 6A showing the multidurometer layers of the tip and shaft.
Figure 6C:
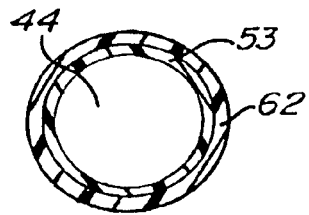
Figure 6D:

FIG. 6A is a perspective view of atraumatic tip 18B coupled to elongated shaft 12B. FIGS. 6B, 6C, and 6D illustrate section views of atraumatic tip 18B taken along section lines B-B, C-C, and D-D showing the multidurometer layers of atraumatic tip 18B and elongated shaft 12B. In particular, and as shown in FIG. 6B, the section of the delivery system taken along section B-B includes outer portion 62 of atraumatic tip 12B, central portion 53 of atraumatic tip 12B, wall 64 of elongated shaft 12B, inner wall lining 66 of wall 64, and elongated shaft lumen 44. As discussed above, outer and central portions 62 and 53 are preferably formed from 35 D PEBAX and 40 D PEBAX, respectively. Furthermore, wall 64 is preferably formed from 72 D PEBAX, and liner 66 is preferably formed from a PTFE material such as Teflon.

As shown in FIGS. 6A and 6B, wall 64 of elongated shaft 12B may optionally be reinforced with mesh 68. Mesh 68 may provide several advantages, including but not limited to making elongated shaft 12B kink resistant, providing longitudinal rigidity to limit the amount that elongated shaft 12B may stretch, and helping to provide improved steering of elongated shaft 12B within a body lumen. Mesh 68 may be formed from numerous materials including, but not limited to, platinum, stainless steel, and Nitinol.

Figure 7A:
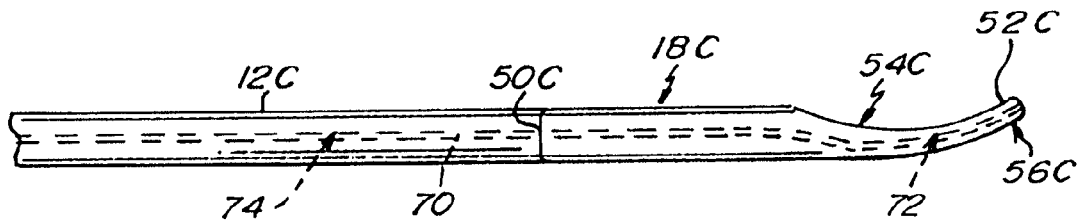
FIG. 7A is a side view of a third alternative embodiment of an atraumatic tip in accordance with the present invention having an internal wire support.

FIGS. 7A and 7B illustrate side and top views, respectively, of atraumatic tip 18C, which is a third alternative embodiment of an atraumatic tip in accordance with the present invention. In particular, and as shown in FIG. 7A, atraumatic tip 18C has a shovel nose type design with internal wire support 70 extending longitudinally along opposing sides of the tip and into elongated shaft 12C, which may be formed integral with atraumatic tip 18C. Internal wire support 70 includes curved distal section 72 and generally straight proximal section 74, and is designed to allow atraumatic tip 18C to bend or flex as is contacts, for example, an inner wall of a body lumen, while preventing the tip or the distal portion of elongated shaft 12C from bending so much that slanted facial opening 54C becomes substantially blocked.

As illustrated in the top view shown in FIG. 7B, internal wire support 70 is looped around distal end 52C of atraumatic tip 18C to reinforce the tip region. Furthermore, internal wire support 70 is shown completely encased within the tip, although one skilled in the art would appreciate that a portion of Internal wire support 70 may be exposed in other embodiments. Internal wire support 70 may be formed from numerous materials such as a shape memory alloy like Nitinol. Furthermore, internal wire support 70 may be encased in various materials. However, a plastic resin material such as a PEBAX material is preferred.

FIG. 8 is a side view of atraumatic tip 18D, which is a fourth alternative embodiment of an atraumatic tip in accordance with the present invention. As shown in FIG. 8, elongated shaft 12D is reinforced with braid 68D, which is similar to braid 68 discussed above in reference to FIGS. 6A and 6B, while atraumatic tip 18D is reinforced with coil 72. Coil 72 is designed such that atraumatic tip 18D is flexible but also kink resistant. In FIG. 8, coil 72 ends a distance D from a proximal end of slanted facial opening 54D. However, embodiments wherein coil 72 ends either a shorter or longer distance from the proximal end of slanted facial opening 54D are also contemplated. One advantage of reinforcing atraumatic tip 18D with a coil member instead of a braid member is that a coil may be more flexible than a braid. In other embodiments, coil 72 may be tapered (i.e., have a decreased thickness) to increase flexibility toward distal end 52D of atraumatic tip 18D.

FIG. 9 is a side view of atraumatic tip 18E, which is a fifth alternative embodiment of an atraumatic tip in accordance with the present invention. Atraumatic tip 18E includes guide wire 74, which is bonded to or encased within the walls defining atraumatic tip 18E and extends longitudinally along the tip and past distal end 52E. Guide wire 74 includes curved flange 76. Flange 76 is a flexible member designed to deflect when it comes into contact with, for example, an inner wall of a body lumen, to help guide elongated shaft 12E through the body lumen without puncturing or otherwise damaging the lumen. Distal portion 78 of flange 76 may be formed from the guide wire itself, or alternatively it may be formed by, for example, creating a build-up of solder, an epoxy material, or a plastic material on flange 76.

Near the junction of atraumatic tip 18E and elongated shaft 12E, guide wire 74 forms a coil region 80 designed to reinforce elongated shaft 12E. Thus, as shown in FIG. 9, a single piece of guide wire 74 forms both curved flange 76 and coil region 80. However, one skilled in the art would appreciate that curved flange 76 and coil region 80 may be formed from separate pieces of wire without departing from the intended scope of the present invention.

Optionally, and as illustrated in FIG. 9, the portion of guide wire 74 within atraumatic tip 18E between proximal end 50E and distal end 52E may be tapered such that the diameter of guide wire 74 near coil region 80 is greater than the diameter of guide wire 74 near flange 76. As a result of tapering guide wire 74, atraumatic tip 18E may be more flexible toward distal end 52E and less flexible toward proximal end 50E.

Figure 10:
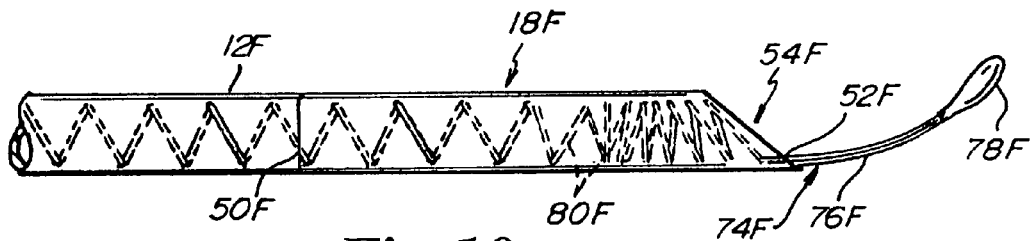
FIG. 10 is a side view of a sixth alternative embodiment of an atraumatic tip in accordance with the present invention having a variable pitch coil reinforcing means.

FIG. 10 is a side view of atraumatic tip 18F, which is a sixth alternative embodiment of an atraumatic tip in accordance with the present invention. Atraumatic tip 18F is similar to atraumatic tip 18E, and includes guide wire 74F having curved wire flange 76F, distal portion 80F, and coil region 80F. However, instead of coil region 80F beginning near the junction of atraumatic tip 18F and elongated shaft 12F, coil region 80F begins near slanted facial opening 54F and extends proximally through atraumatic tip 18F and into elongated shaft 12F. Thus, both atraumatic tip 18F and elongated shaft 12F are reinforced by a helical wire coil.

As shown in FIG. 10, the helical wire that forms coil region 80F has a variable pitch design. In particular, the pitch of coil region 80F is greater near elongated shaft 12F and less near distal end 52F of atraumatic tip 18F. As a result, atraumatic tip 18F is generally more flexible than elongated shaft 12F. One skilled in the art would appreciate that coil region 80F represents merely one example of a coil region with a variable pitch, and that coil regions having numerous other pitch configurations are possible and within the intended scope of the present invention.

Figure 11A:
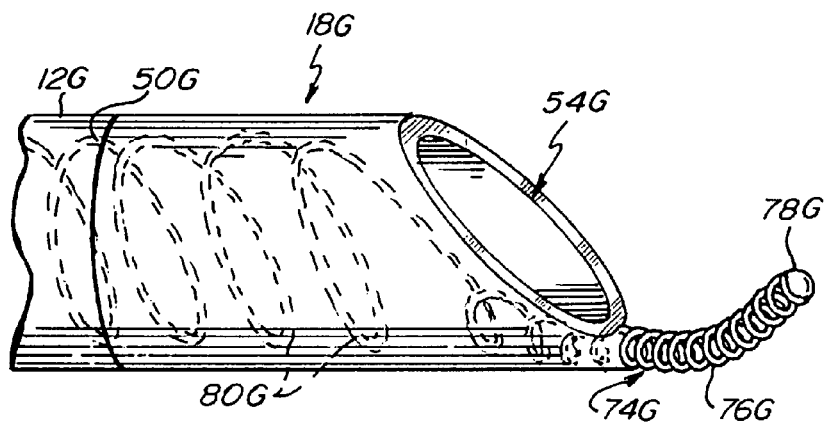
FIG. 11A is a side view of a seventh alternative embodiment of an atraumatic tip in accordance with the present invention having a coil flange extending from a distal end of the tip.

FIG. 11A is a side view of atraumatic tip 18G, which is a seventh alternative embodiment of an atraumatic tip in accordance with the present invention. Atraumatic tip 18G is similar to atraumatic tip 18F, and includes guide wire 74G having curved flange 76G, distal portion 78G, and coil region 80G. However, unlike flange 76F, flange 76G is formed into a second, smaller diameter coil region. In particular, the coiled flange 76G and coil region 80G are preferably formed from one continuous piece of wire, although the two regions may be formed from separate pieces of wire without departing from the intended scope of the present invention. Because of its spring properties, coiled flange 76G is able to help absorb the impact when atraumatic tip 18G contacts, for example, an inner wall of a body lumen, to help guide elongated shaft 12G through the body lumen. Distal portion 78G, which is shown in FIG. 11A as a semicircular element, helps to prevent perforation of the body lumen by flange 76G.

Figure 11B:
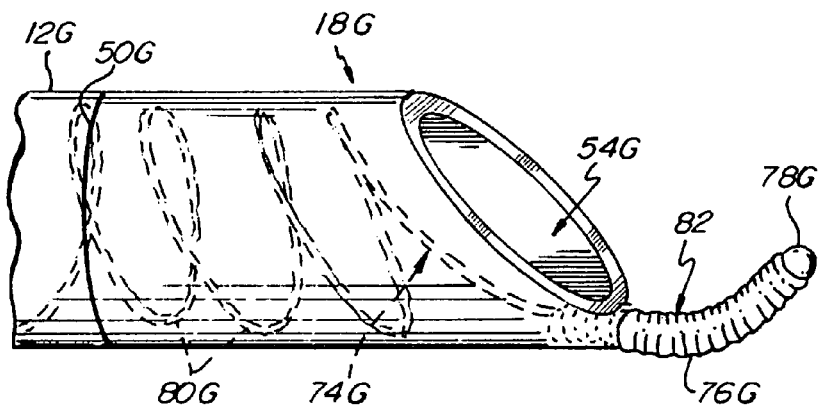
FIG. 11B is a side view of the atraumatic tip illustrated in FIG. 11A, further including a cover member configured to cover the coil flange.

Optionally, atraumatic tip 18G may further include coil cover 82 over the coiled flange 76G, as illustrated in FIG. 11B. Coil cover 82 is designed to minimize the chance that an occlusive device delivered through atraumatic tip 18G may become hooked or caught on coiled flange 76G. Coil cover 82 may be formed form numerous materials, including but not limited to PEBAX, Terylene, or Teflon.

Figure 12:
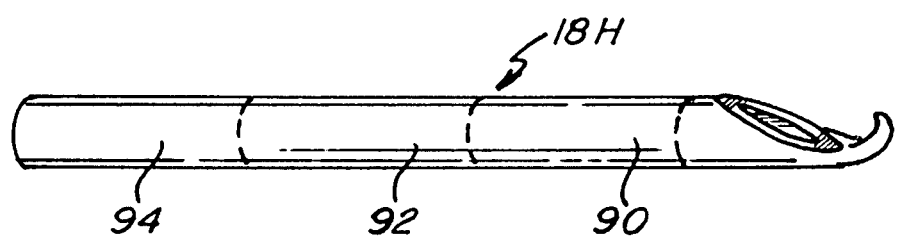
FIG. 12 is a side view of an eighth alternative embodiment of an atraumatic tip in accordance with the present invention illustrating a multidurometer tip design.

FIG. 12 is a side view of atraumatic tip 18H, which is an eighth alternative embodiment of an atraumatic tip in accordance with the present invention. Atraumatic tip 18H includes distal tip portion 90, mid tip portion 92, and proximal tip portion 94. In order to create a tip with varying flexibility, portions 90, 92, and 94 may be formed from different materials having different material properties. Thus, for example, distal tip portion 90 may be formed from a soft PEBAX material, mid tip portion 92 may be formed from a stiffer PEBAX material, and proximal tip portion may be formed from an even stiffer PEBAX material. Thus, the end result is a tip with varying flexibility. It should be noted that atraumatic tip 18G was divided into three portions formed from three different materials for purposes of example only. Thus, tips in accordance with the present invention may include any number of separate portions formed from one or more different materials.

As shown and described in reference to FIG. 12, atraumatic tip 18H includes three distinct portions formed from three distinct materials. Alternatively, atraumatic tip 18H may be extruded in a manner such that instead of having a single transition point between materials, there is a gradual transition from one material to another. For instance, a longitudinal length of proximal tip portion 94 may initially contain 72 D PEBAX, but gradually transition to 35 D PEBAX prior to reaching mid tip portion 92. This type of design allows for a gradual transition between materials, which in turn creates a gradual change in tip flexibility.

Figure 13:
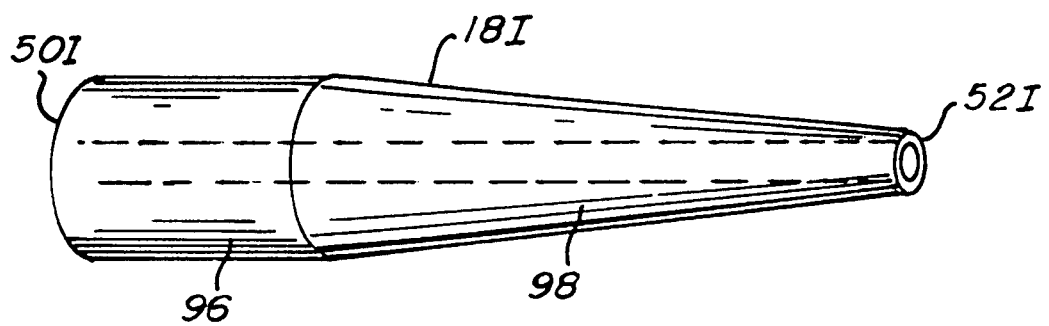
FIG. 13 is a side view of a ninth alternative embodiment of an atraumatic tip in accordance with the present invention having a variable tip wall thickness.

FIG. 13 is a side view of atraumatic tip 18I, which is a ninth alternative embodiment of an atraumatic tip in accordance with the present invention. Atraumatic tip 18I includes proximal portion 96 and distal portion 98. Atraumatic tip 18I is similar to atraumatic tip 18H in that flexibility of the tip varies longitudinally along the tip. However, unlike atraumatic tip 18H which achieves variable flexibility by varying the type of tip material, atraumatic tip 18I achieves variable flexibility by varying wall thickness (i.e., tapering the tip). As shown in FIG. 13, assuming a constant lumen diameter, wall thickness decreases as you move longitudinally from proximal end 50I toward distal end 52I of atraumatic tip 18I. As a result, distal end 52I will have a greater flexibility than proximal end 50I.

One skilled in the art would appreciate that although the majority of the atraumatic tip embodiments were described in reference to a delivery system such as delivery system 10A that functions with self-expanding occluding devices, these embodiments could be incorporated into tips for delivery systems, such as delivery system 10, that function with non self-expanding occluding devices as well.

The present invention may be embodied in other specific forms without departing from the spirit of the essential attributes thereof; therefore, the illustrated embodiments should be considered in all respects as illustrative and not restrictive.

What is claimed is:

1. A delivery system comprising:
   an elongated catheter shaft having a proximal end and a distal end, the distal end insertable into a body lumen;
   a delivery means for delivering an occluding device to a desired location within the body lumen; and
   a flexible atraumatic tip on the distal end of the elongated catheter shaft for guiding the elongated catheter shaft through the body lumen, the atraumatic tip having a proximal end coupled onto an outer surface of the distal end of the elongated catheter such that the distal end of the elongated catheter is inside the atraumatic tip, a distal end having a distal leading edge, a slanted facial opening near the distal end of the atraumatic tip, and a flexible elongated portion extending from a distal end of the slanted facial opening to the distal leading edge, wherein the flexible elongated portion is formed with a bend that extends away from a longitudinal length of the flexible atraumatic tip in a direction substantially consonant with the slanted facial opening from about the distal end of the slanted facial opening to the distal leading edge such that, with regard to relative positions to each other, the distal leading edge is located below the distal end of the slanted facial opening and the occluding device is deployed above the distal leading edge.

2. The delivery system of claim 1, wherein the occluding device includes a self-expanding tubular member deployable from a collapsed position within a lumen of the elongated catheter shaft to an expanded position outside of the elongated catheter shaft.

3. The delivery system of claim 2, wherein the delivery means comprises a pusher rod slidably received within the lumen of the elongated catheter shaft.

4. The delivery system of claim 1, wherein the elongated catheter shaft is insertable into a working port of an endoscope.

5. The delivery system of claim 1, wherein the elongated catheter shaft is insertable into a working port of a hysteroscope.

6. The delivery system of claim 1, wherein the atraumatic tip comprises a tubular member.

7. The delivery system of claim 6, wherein the slanted facial opening has a generally ovoid configuration.

8. The delivery system of claim 6, wherein the distal leading edge is blunt.

9. The delivery system of claim 8, wherein the blunt distal leading edge has a generally rounded outer face.

10. The delivery system of claim 1, wherein the atraumatic tip is bendable about midway up a longitudinal length of the slanted facial opening.

11. A delivery system comprising:
an elongated catheter shaft having a proximal end and a distal end, the distal end insertable into a body lumen;
a delivery means for delivering an occluding device to a desired location within the body lumen; and
an atraumatic tip on the distal end of the elongated catheter shaft for guiding the elongated catheter shaft through the body lumen, the atraumatic tip having a proximal end coupled onto an outer surface of the distal end of the elongated catheter such that the distal end of the elongated catheter is inside the atraumatic tip, a distal end, a slanted facial opening near the distal end of the atraumatic tip, and a flexible elongated portion extending from a distal end of the slanted facial opening to the distal end of the atraumatic tip, wherein the flexible elongated portion is formed with a bend that extends away from a longitudinal length of the flexible atraumatic tip in a direction substantially consonant with the slanted facial opening from about the distal end of the slanted facial opening to the distal end of the atraumatic tip such that, with regard to relative positions to each other, the distal end of the atraumatic tip is located below the distal end of the slanted facial opening and the occluding device is deployed above the distal end of the atraumatic tip.

12. The delivery system of claim 11, wherein the atraumatic tip is bendable about midway up a longitudinal length of the slanted facial opening.

13. A delivery system comprising:
an elongated catheter shaft having a proximal end and a distal end, the distal end insertable into a body lumen; and
a flexible atraumatic tip on the distal end of the elongated catheter shaft for guiding the elongated catheter shaft through the body lumen, the atraumatic tip having a proximal end coupled onto an outer surface of the distal end of the elongated catheter such that the distal end of the elongated catheter is inside the atraumatic tip, a distal end having a distal leading edge, a slanted facial opening near the distal end of the atraumatic tip, and a flexible elongated portion extending from a distal end of the slanted facial opening to the distal leading edge, wherein the flexible elongated portion is formed with a bend that extends away from a longitudinal length of the flexible atraumatic tip in a direction substantially consonant with the slanted facial opening from about the distal end of the slanted facial opening to the distal leading edge such that, with regard to relative positions to each other, the distal leading edge is located below the distal end of the slanted facial opening.

14. The delivery system of claim 13, wherein the atraumatic tip comprises a tubular member.

15. The delivery system of claim 14, wherein the slanted facial opening has a generally ovoid configuration.

16. The delivery system of claim 14, wherein the distal leading edge is blunt.

17. The delivery system of claim 16, wherein the blunt distal leading edge has a generally rounded outer face.

\* \* \* \* \*